(12) United States Patent
Besser et al.

(10) Patent No.: US 9,827,169 B2
(45) Date of Patent: *Nov. 28, 2017

(54) NASOGASTRIC TUBE WITH CAMERA

(71) Applicant: NUTRISEAL L.P., Tel Aviv (IL)

(72) Inventors: Doron Besser, Tel Aviv (IL); Guy Ben Ezra, Karkur (IL)

(73) Assignee: NUTRISEAL L.P., Tel Aviv (IL)

( * ) Notice: Subject to any disclaimer, the term of this patent is extended or adjusted under 35 U.S.C. 154(b) by 588 days.

This patent is subject to a terminal disclaimer.

(21) Appl. No.: 14/556,501

(22) Filed: Dec. 1, 2014

(65) Prior Publication Data

US 2015/0174013 A1 Jun. 25, 2015

Related U.S. Application Data

(63) Continuation-in-part of application No. 14/098,426, filed on Dec. 5, 2013, now Pat. No. 9,763,856, which
(Continued)

(51) Int. Cl.
*A61J 15/00* (2006.01)
*A61B 1/05* (2006.01)
(Continued)

(52) U.S. Cl.
CPC ............. *A61J 15/003* (2013.01); *A61B 1/042* (2013.01); *A61B 1/05* (2013.01); *A61B 1/0676* (2013.01);
(Continued)

(58) Field of Classification Search
CPC ...... A61B 17/3478; A61B 2017/00269; A61B 2017/306; A61F 2/04; A61F 5/0069;
(Continued)

(56) References Cited

U.S. PATENT DOCUMENTS 5,389,074 A 2/1995 Parker et al.
5,707,351 A * 1/1998 Dorsey, III ......... A61M 1/0062
604/30
(Continued)

FOREIGN PATENT DOCUMENTS

EP 2301512 3/2011
EP 2301512 A2 * 3/2011 ............ A61J 15/003
(Continued)

*Primary Examiner* — Bhisma Mehta
*Assistant Examiner* — William Frehe
(74) *Attorney, Agent, or Firm* — The Roy Gross Law Firm, LLC; Roy Gross

(57) ABSTRACT

A system comprising: a nasogastric tube comprising: (a) a main lumen having one or more proximal connectors for connecting to a source of substances or pressure, (b) at least four vacuum lumens peripherally surrounding said main lumen, (c) at least four suction ports for sealingly drawing an inner wall of an esophagus thereagainst, each of said at least four suction ports associated with a different one of said four vacuum lumens, wherein said at least four suction ports are distributed between at least two different locations along a longitudinal axis of said nasogastric tube; and an imaging system for capturing and rendering one or more images of an area accessible by said tube, said imaging system comprising: (d) a camera disposed at a distal end of said nasogastric tube, for capturing said images; (e) an illuminator disposed at said distal end of said nasogastric tube, and (f) a processing unit provided at a proximal end of said nasogastric tube, that is configured to receive and process said captured images, render said processed images on a display screen, and provide a camera control signal to control said camera and a light control signal to control said illuminator.

29 Claims, 11 Drawing Sheets

Related U.S. Application Data is a continuation-in-part of application No. 13/962,289, filed as application No. PCT/US2012/046850 on Jul. 16, 2012.

(60) Provisional application No. 61/508,670, filed on Jul. 17, 2011.

(51) Int. Cl.
*A61B 1/06* (2006.01)
*A61B 1/04* (2006.01)

(52) U.S. Cl.
CPC ....... *A61J 15/0003* (2013.01); *A61J 15/0073* (2013.01); *A61J 15/0092* (2013.01)

(58) Field of Classification Search
CPC .............. A61M 39/22; A61M 39/223; A61M 2039/224; A61J 15/003; A61J 15/0003
USPC ......................................... 604/334, 43, 93.01
See application file for complete search history.

(56) References Cited

U.S. PATENT DOCUMENTS

| | | | |
|---|---|---|---|
| 6,695,764 B2* | 2/2004 | Silverman | A61F 2/04 600/29 |
| 7,399,304 B2 | 7/2008 | Gambale | |
| 8,100,874 B1 | 1/2012 | Jordan et al. | |
| 2003/0208209 A1 | 11/2003 | Gambale et al. | |
| 2004/0153098 A1 | 8/2004 | Chin et al. | |
| 2004/0220515 A1 | 11/2004 | Constantz | |
| 2005/0059962 A1* | 3/2005 | Phan | A61B 18/1492 606/41 |
| 2009/0306626 A1 | 12/2009 | Sinha et al. | |
| 2011/0046653 A1* | 2/2011 | Addington | A61B 5/04882 606/196 |
| 2013/0310806 A1 | 11/2013 | Nevler et al. | |
| 2014/0188080 A1 | 7/2014 | Besser et al. | |

FOREIGN PATENT DOCUMENTS

| | | |
|---|---|---|
| WO | 2003034976 | 5/2013 |
| WO | 2015198297 | 12/2015 |

* cited by examiner

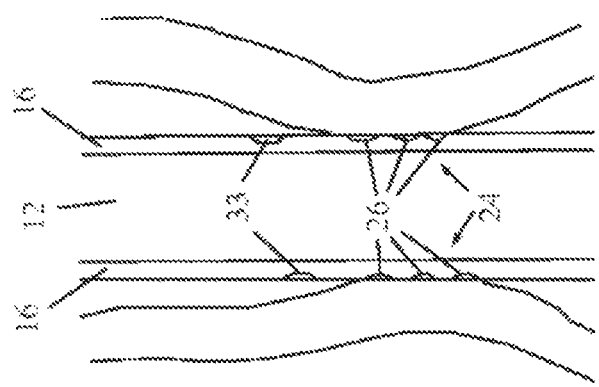

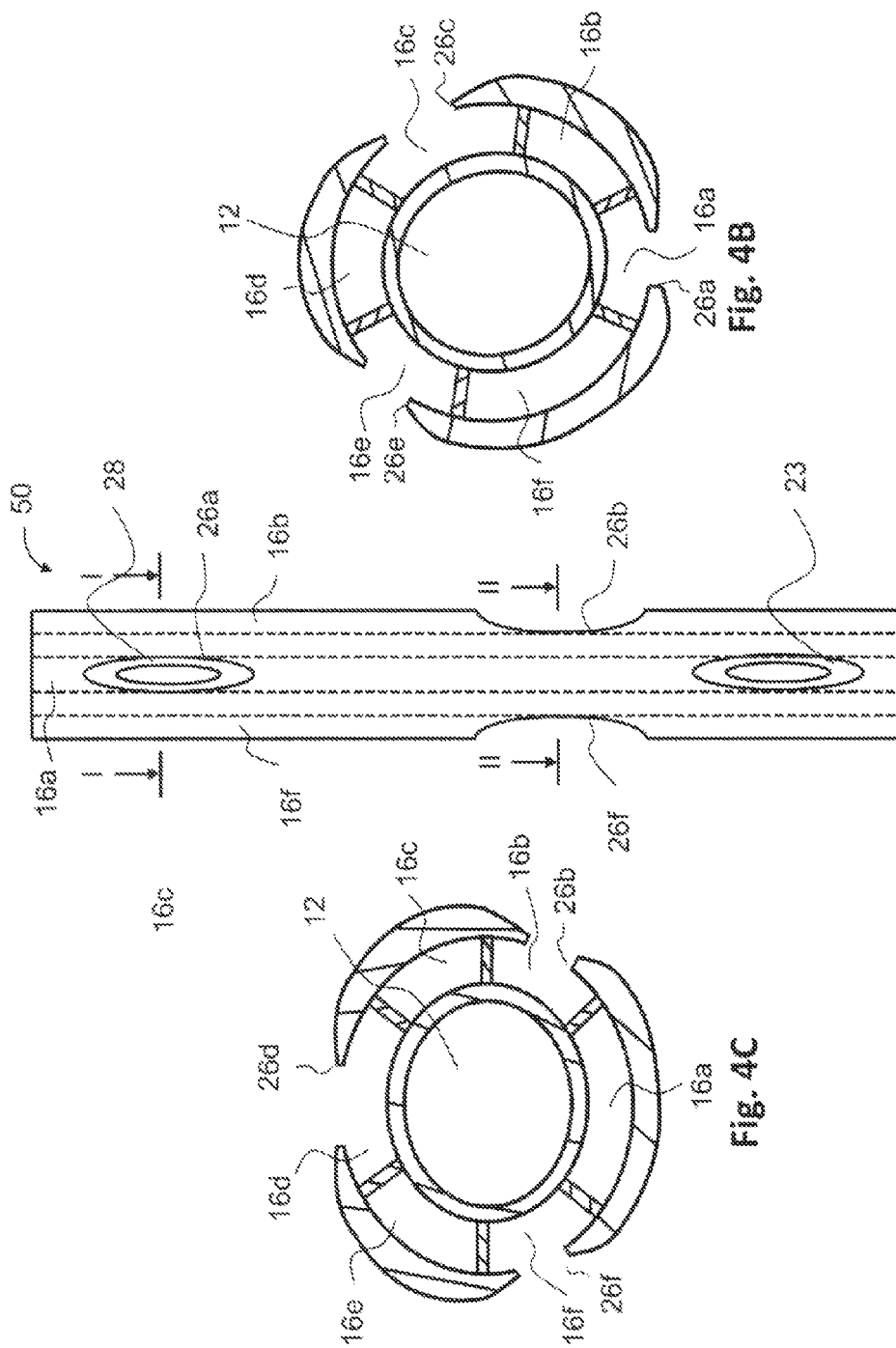

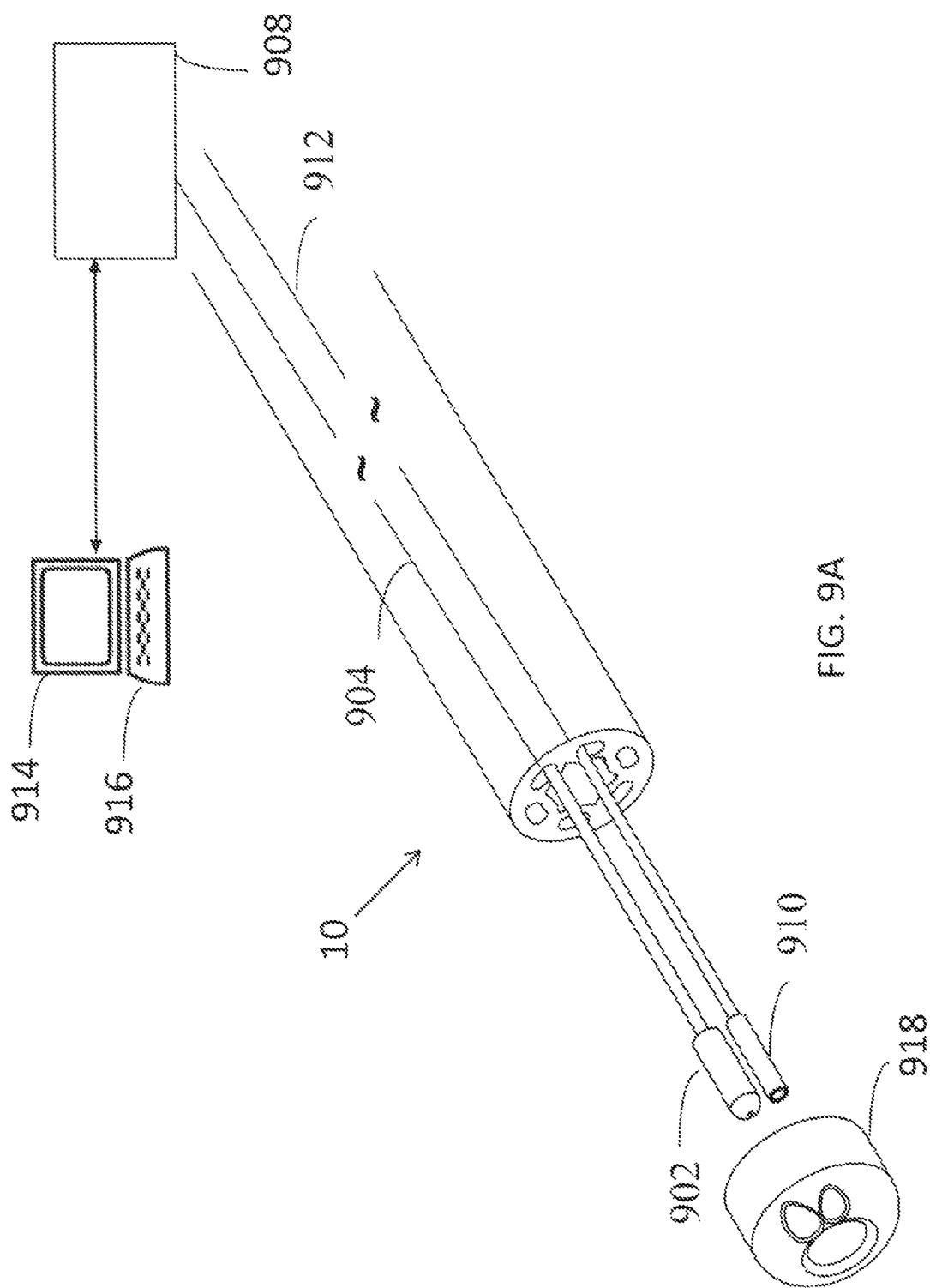

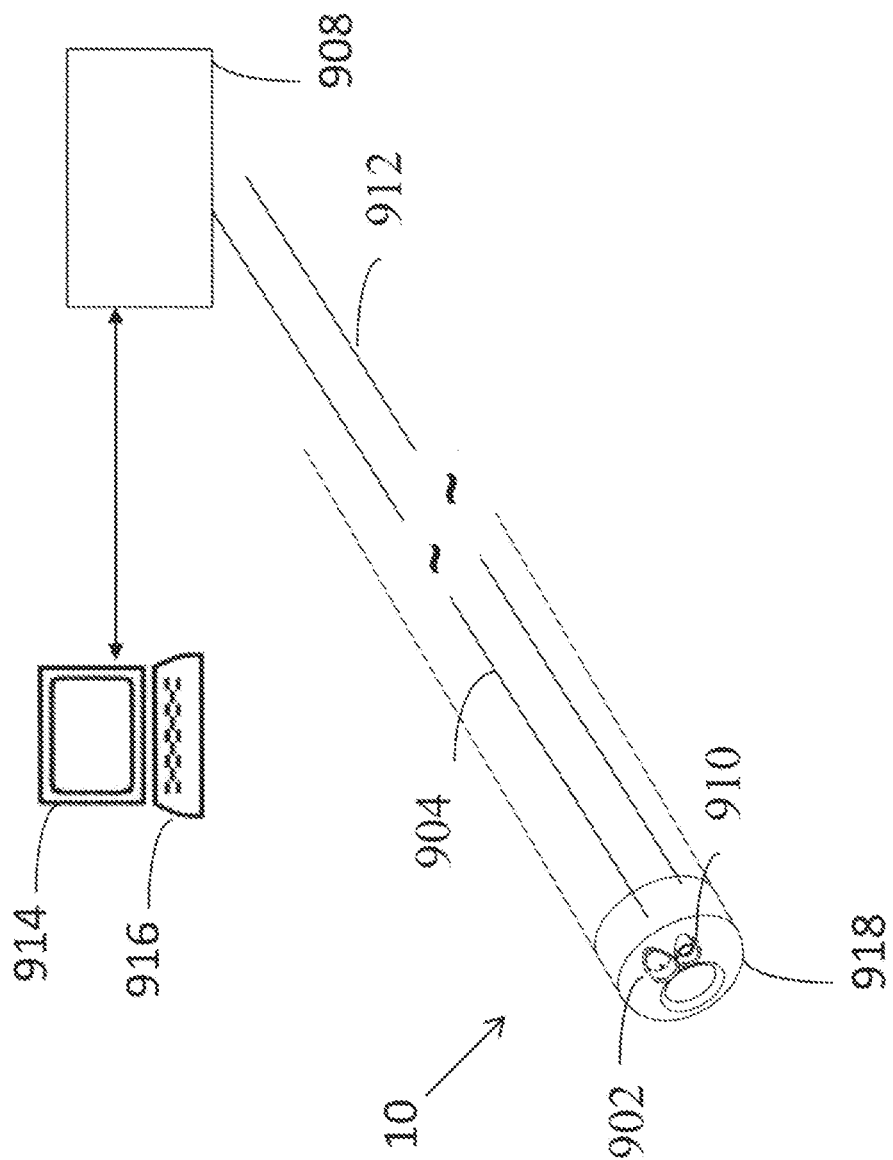

NASOGASTRIC TUBE WITH CAMERA

FIELD OF THE INVENTION

The present invention relates generally to nasogastric tubes.

BACKGROUND OF THE INVENTION

Enteral feeding is a form of hyperalimentation and metabolic support in which nutrient formulas or medicaments are delivered directly to the GI tract, either to the stomach or the duodenum. A nasogastric tube (NGT) is used for feeding and administering drugs and other oral agents. The tube is inserted into the patient's esophagus and stomach in order to ensure the passage of the agents into the stomach and not into the lungs. The NGT can also be used for suction of fluids from the stomach.

However, the use of NGTs can have disadvantages. Minor complications include nose bleeds, sinusitis, and a sore throat. Sometimes more significant complications occur including erosion of the nose where the tube is anchored, esophageal perforation, pulmonary aspiration, a collapsed lung, or intracranial placement of the tube.

Even worse, during feeding, excessive gastric pressure may result. From time to time, the body relieves such excess gastric pressure by expelling gas or liquid or reflux fluid. The fluids are expelled from the stomach through the esophagus to the mouth or nasal pathways. The reflux fluids may be inhaled into the lungs with possible risk of aspiration pneumonia, bacterial infection in the pharynx or esophagus or any other ailments. Accordingly, numerous studies have linked the use of the NGT to an increase in ventilator-associated pneumonia (VAP). VAP is the most common nosocomial infection in the intensive care unit (ICU), and it is associated with prolonged hospitalization, increased health care costs, and high attributable mortality.

There thus exists a pressing need for an NGT that is capable of significantly reducing the risk of reflux food and developing VAP.

SUMMARY OF THE INVENTION

The following embodiments and aspects thereof are described and illustrated in conjunction with systems, tools and methods which are meant to be exemplary and illustrative, not limiting in scope.

There is provided, in accordance with an embodiment, a system comprising: a nasogastric tube comprising: (a) a main lumen having one or more proximal connectors for connecting to a source of substances or pressure, (b) at least four vacuum lumens peripherally surrounding said main lumen, (c) at least four suction ports for sealingly drawing an inner wall of an esophagus thereagainst, each of said at least four suction ports associated with a different one of said at least four vacuum lumens, wherein said at least four suction ports are distributed between at least two different locations along a longitudinal axis of said nasogastric tube; and an imaging system for capturing and rendering one or more images of an area accessible by said nasogastric tube, wherein said imaging system comprises: (d) a camera that is disposed at a distal end of said nasogastric tube for capturing said images; (e) an illuminator that is disposed at said distal end of said nasogastric tube for illuminating an area surrounding said camera; and (f) a processing unit that is provided at a proximal end of said nasogastric tube and configured to receive and process said captured images, render said processed images on a display screen, and provide a camera control signal to control said camera and a light control signal to control said illuminator.

In some embodiments, the system further comprises a camera cable connecting said camera to said processing unit, wherein said images and said camera control signal are transmitted via said camera cable; and a light cable connecting said illuminator to said processing unit, wherein said light control signal is transmitted via said light cable.

In some embodiments, said camera cable and said light cable are housed in any of said at least four vacuum lumens.

In some embodiments, the system further comprises an orientation adjustor controlling the orientation of said camera.

In some embodiments, the system further comprises a control panel for applying said camera control signal and said light control signal.

In some embodiments, the system further comprises a vacuum source connected to said at least four vacuum lumens.

In some embodiments, said at least four vacuum lumens are connected to said vacuum source via a pressure regulator and a valve.

In some embodiments, said main lumen and said at least four vacuum lumens are constructed as one unit.

In some embodiments, said at least four vacuum lumens are a separate unit from said main lumen, and wherein said at least four vacuum lumens are slidable relative to said main lumen.

In some embodiments, said main lumen and said at least four vacuum lumens are arranged as concentrically arranged conduits.

In some embodiments, the system further comprises one or more auxiliary suction ports proximal to said at least four suction ports.

In some embodiments each of said at least four suction ports comprises a graduated edging.

In some embodiments, the system further comprises a manifold configured to connect said at least four vacuum lumens to said valve.

In some embodiments, said manifold is transparent.

In some embodiments, said at least four vacuum lumens comprise at least six vacuum lumens.

In some embodiments, at least one of said at least four suction ports comprises two or more suction ports, successively arranged along a portion of a longitudinal axis of said nasogastric tube.

In some embodiments, said nasogastric tube further comprises two or more longitudinal radiopaque stripes.

In some embodiments, said two or more longitudinal radiopaque stripes are embedded in an outer wall of said nasogastric tube.

In some embodiments, the system further comprises at least one gastric decompression port associated with an additional at least one vacuum lumen, wherein said at least one gastric decompression port is disposed distally to said at least two different locations along said length of said nasogastric tube.

In some embodiments, said at least four suction ports are positioned on a circumference extension of said main lumen and have a concavity whose longitudinal cross-section have a shape delimited between (i) a first arc of a first circle, the first arc having a length of 25 millimeters and a height of 1.5 millimeters, and (ii) a second arc of a second circle, the second arc having a length of 15 millimeters and a height of 1 millimeter.

In some embodiments, each of said at least four vacuum lumens is substantially rectangular shaped.

In some embodiments, each of said at least four vacuum lumens has a width-height aspect ratio of 1:1 to 3:1.

In some embodiments, each of said at least four vacuum lumens has a height of 0.3-0.8 mm.

In some embodiments, each of said at least four vacuum lumens has a width of at most 1.5 mm.

There is provided, in accordance with an embodiment, a method comprising: introducing a nasogastric tube into an esophagus of a patient, said nasogastric tube comprising a main lumen having one or more proximal connectors for connecting to a source of substances or pressure, four or more vacuum lumens peripheral to said main lumen, four or more suction ports, each of said four or more suction ports associated with a different one of said four or more vacuum lumens, wherein said four or more suction ports are distributed between at least two different locations along said nasogastric tube, and a camera and illuminator disposed at a distal end of said nasogastric tube; applying vacuum interchangeably to said four or more vacuum lumens so as to sealingly draw an inner wall of an esophagus thereagainst, each time in a different location along said esophagus; capturing an image by said camera of an area illuminated by said illuminator; transmitting said captured image to a processing unit; and processing and rendering said image on a display unit.

In some embodiment, the method further comprises adjusting a positioning of said nasogastric tube in response to said rendered image.

In some embodiment, the method further comprises adjusting an orientation of said camera via an orientation adjustor, in response to said rendered image.

In some embodiment, the method further comprises adjusting an intensity of said illuminator, in response to said rendered image.

In some embodiment, the method further comprises regulating the vacuum so that a suction level is not constant over time.

In some embodiment, the method further comprises regulating vacuum to said four or more suction ports of said four or more vacuum lumen, so as to create peristaltic movement or other oscillatory movement of the esophagus.

In some embodiment, said applying of the vacuum restricts at least 60% of passage through the esophagus.

In some embodiment, said four or more suction ports comprise graduated edging.

In some embodiment, said four or more vacuum lumens are connected to said source via a pressure regulator and a valve.

In some embodiment, the method further comprises visually monitoring a transparent manifold coupling said four or more vacuum lumens with said valve for backflow of gastric substances.

In some embodiment, at least one suction port of said four or more suction ports comprises two or more suction ports, successively arranged along a portion of a longitudinal axis of said nasogastric tube.

In some embodiment, the method further comprises applying a vacuum for decompressing gastric gas via at least one gastric decompression port disposed distally to the at least two different locations along the length of said nasogastric tube.

In some embodiment, each of said four or more suction ports has a concavity whose longitudinal cross-section has a shape delimited between (i) a first arc of a first circle, the first arc having a length of 25 millimeters and a height of 1.5 millimeters, and (ii) a second arc of a second circle, the second arc having a length of 15 millimeters and a height of 1 millimeter.

In some embodiment, each of said at least four vacuum lumens is substantially rectangular shaped.

In some embodiment, each of said at least four vacuum lumens has a width-height aspect ratio of 1:1 to 3:1.

In some embodiment, each of said at least four vacuum lumens has a height of 0.3-0.8 mm.

In some embodiment, each of said at least four vacuum lumens has a width of at most 1.5 mm.

In addition to the exemplary aspects and embodiments described above, further aspects and embodiments will become apparent by reference to the figures and by study of the following detailed description.

BRIEF DESCRIPTION OF THE DRAWINGS

The present invention will be understood and appreciated more fully from the following detailed description taken in conjunction with the drawings in which:

FIG. 3 is a simplified schematic illustration of the nasogastric tube being used to suck and seal the inner wall of the esophagus against the NGT, in accordance with an embodiment of the present invention;

FIG. 4A is a simplified, schematic illustration of a transparent front view of a portion of a nasogastric tube, constructed and operative in accordance with another embodiment of the present invention;

FIG. 4B is a simplified schematic illustration of a cross-section along line I-I of the nasogastric tube of FIG. 4A;

FIG. 4C is a simplified schematic illustration of a cross-section along line II-II of the nasogastric tube of FIG. 4A;

FIGS. 9A-B illustrate an imaging system provided with the NGT, in accordance with an embodiment.

DETAILED DESCRIPTION OF EMBODIMENTS

Figure 1:
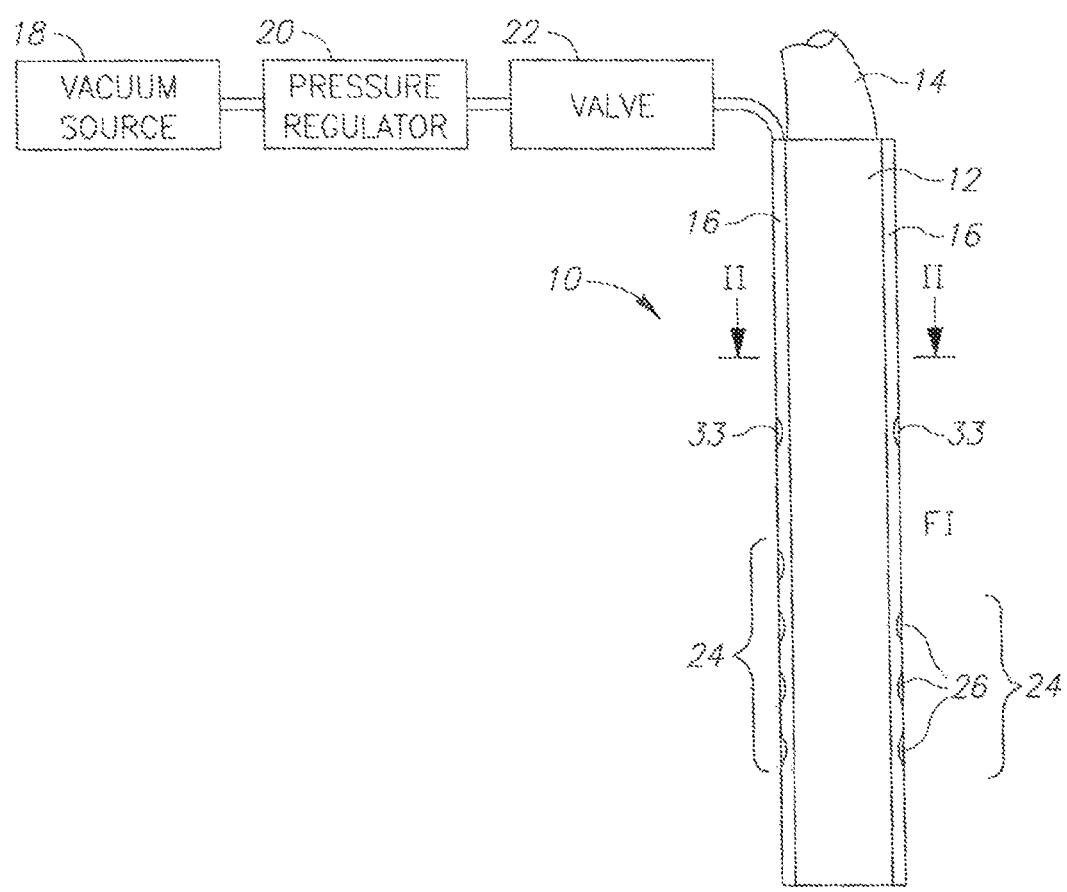
FIG. 1 is a simplified schematic illustration of a nasogastric tube, constructed and operative in accordance with a non-limiting embodiment of the present invention.

The present invention provides an imaging system with a nasogastric tube (NGT) and a method thereof, as is described more in detail hereinbelow. The NGT includes a tube and an imaging system for providing real-time imaging at the distal end of the tube. Additionally, an illuminator is disposed with the imaging system to illuminate the area for which images are captured by the imaging system.

In some embodiment, the NCT is provided with a vacuum control unit. The vacuum control unit couples the esophagus to the tube thus disabling the reflux of the food along the esophagus to the trachea. Furthermore, the structure of an NGT according to the present invention enables locally selective application of the vacuum within the esophagus. Thus, the location of the esophagus coupling to the tube may be changed in time in order to diminish tissue damage to the esophagus.

In some embodiments, a nasogastric tube of the invention comprises at least one vacuum lumen comprising at least one suction port for sealingly drawing an inner wall of an esophagus thereagainst. An NGT according to the present invention can be used in ICU, or elsewhere, in order to reduce the complications associated with reflux such as the risk of VAP and in order to prevent or reduce tissue damage.

Furthermore, the vacuum control unit enables decompression of a subject's abdomen, including but not limited to the stomach or intestines.

According to some embodiments, the NGT of the present invention is configured to perform as a feeding tube as well as a gastric decompression tube. Thus, the NGT enables administration of nutrients or drugs directly to a subject's stomach or intestines and simultaneously or interchangeably enables gastric decompression.

In accordance with an embodiment, the invention provides a system comprising an NGT comprising a feeding mechanism, a suction mechanism configured to sealingly draw an inner wall of an esophagus thereagainst, and a gastric decompression mechanism. In some embodiments, the suction mechanism is further configured to aspirate fluids from the esophagus. As will be described in more detail hereinbelow, the suction mechanism and the gastric decompression mechanism are, in some embodiments, disposed (situated) and associated by one or more same lumens. In other embodiments, the suction mechanism and the gastric decompression mechanism are configured to perform by independent lumens.

According to some embodiments, the NGT is composed of at least one main lumen and a plurality of peripheral lumens, wherein a portion of said plurality of peripheral lumens comprise at least one gastric decompression port and a portion of said plurality of peripheral lumens comprise at least one suction port configured to sealingly draw an inner wall of an esophagus thereagainst.

According to additional embodiments, the NGT is composed of at least one main lumen, one or more lumens comprising at least one gastric decompression port and one or more peripheral lumens comprising at least one suction port configured to sealingly draw an inner wall of an esophagus thereagainst.

Furthermore, the structure of an NGT, according to some embodiments of the present invention, enables locally selective application of the vacuum within the esophagus. Thus, the location of the esophagus coupling to the tube may be changed in time in order to diminish tissue damage to the esophagus.

According to some embodiments, the peripheral (vacuum) lumens are configured to aspirate fluids such as gastric reflux from the esophagus. In some embodiments, said at least one suction port is configured to aspirate fluids from the esophagus. By virtue of applying vacuum to the peripheral lumens of the NGT described herein, the at least one suction port is used for sealingly drawing an inner wall of an esophagus thereagainst and interchangeably or simultaneously aspirate fluids from the esophagus. One skilled in the art will is well capable of determining the vacuum pressure to be applied for sealing the esophagus and/or aspirating fluids from the esophagus.

An NGT according to the present invention can be used in ICU, or elsewhere, in order to reduce the complications associated with reflux such as the risk of VAP and in order to prevent or reduce tissue damage.

According to the present invention, the inner wall of the esophagus is drawn by negative pressure (vacuum) towards and against the outer contour of the NGT. A vacuum control unit, which is connected to the hospital vacuum unit or any other vacuum unit, enables either simultaneous vacuum pressure in one or more suction units of the NGT or changeable vacuum pressure between the different suction units. In this way, the NGT of the present invention prevents reflux and aspiration of substances or liquids into the patient's lungs and prevents tissue damage, while obviating the need to remove and replace the entire device from the patient's esophagus.

In some embodiments, a tube according to the present invention may be used in other locations in the GI tract or in any other body lumen, such as arteries, veins, etc. However, for simplicity of discussion, this tube is referred to throughout the specification as an NGT.

In some embodiments, the structure of an NGT according to the present invention enables locally selective application of the vacuum within the esophagus. In some embodiments, the location of the esophagus coupling to the tube may be changed in time in order to diminish tissue damage to the esophagus.

Figure 2A:
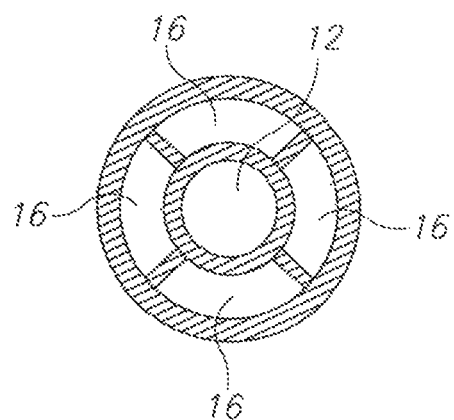
FIG. 2A is a simplified sectional illustration of the NGT of FIG. 1, taken along lines II-II in FIG. 1.

Reference is now made to FIGS. 1 and 2A, which illustrate a nasogastric tube 10, constructed and operative in accordance with a non-limiting embodiment of the present invention.

NGT 10 includes a main (typically, but not necessarily, central) lumen 12. Main lumen 12 may be used to feed and administer drugs and other oral agents, and may also be used for sucking fluids from the stomach. As such, as is known in the art, main lumen 12 may be a double lumen, one lumen for feeding and the other lumen for suction (not to be confused with the vacuum lumens mentioned later). Main lumen 12 is provided with one or more suitable proximal connectors 14 for connecting to a source of substances for feeding or administering, and optionally to a source of pressure (e.g., suction), as is known in the art.

NGT 10 includes one or more vacuum lumens 16 that peripherally surround main lumen 12. The term "peripherally surround" as used in the description and claims, encompasses continuous surrounding (no gaps between the vacuum lumens or one continuous, peripheral vacuum lumen) and discontinuous surrounding (wherein there are separations between discrete vacuum lumens).

Vacuum lumens 16 may be coupled with a vacuum source 18, such as via a pressure regulator 20 and a valve 22, which form a vacuum control unit.

In one embodiment, illustrated in FIG. 2A, there are four vacuum lumens 16 peripherally spaced around main lumen 12; In another embodiment, illustrated in FIG. 2B, there are six vacuum lumens 16 peripherally spaced around main lumen 12; the invention is not limited to this number of vacuum lumens. The vacuum lumens 16 may be equally or unequally spaced from each other. Main lumen 12 and vacuum lumens 16 are thus arranged as concentrically arranged conduits. Vacuum lumens 16 are coupled with a vacuum source 18, such as via a pressure regulator 20 and a valve 22, which form a vacuum control unit.

In some embodiments, a nasogastric tube of the invention comprises at least one vacuum lumen comprising at least one suction port for sealingly drawing an inner wall of an esophagus thereagainst, said at least one vacuum lumen has a width (Ws)-height (Hs) aspect ratio of 1:1 to 3:1. In another embodiment, said width (Ws)-height (Hs) aspect ratio of the vacuum lumen is at least 1:1 or at least 2:1. In another embodiment, said width (Ws)-height (Hs) aspect ratio of the vacuum lumen is at most 4:1 or at most 3:1.

In another embodiment, said one or more vacuum lumen(s) have a height Hs of 0.3-0.8 mm. In another embodiment, said one or more vacuum lumen(s) has a height Hs of at most 1, at most 0.9 mm, at most 0.8 mm, at most 0.75 mm or at most 0.7 mm. In another embodiment, said one or more vacuum lumen(s) has a height Hs of at least 0.3, at least 0.4, at least 0.5 mm, at least 0.6 mm, at least 0.65 or at least 0.7 mm.

In another embodiment, said one or more vacuum lumens have a width Ws of at most 4 mm, at most 3 mm, at most 2.5 mm, at most 2 mm, at most 1.9 mm, at most 1.8 mm, at most 1.7 mm, at most 1.6 mm, at most 1.5 mm or at most 1.5 mm. In another embodiment, said one or more vacuum lumens have a width Ws of at most 1.5 mm. In another embodiment, said one or more vacuum lumens have a width Ws of at least 0.5 mm, at least 0.6 mm, at least 0.7 mm, at least 0.8, at least 0.9, at least 1 mm, at least 1.1 mm, at least 1.2 mm or at least 1.3 mm.

Figure 2B:
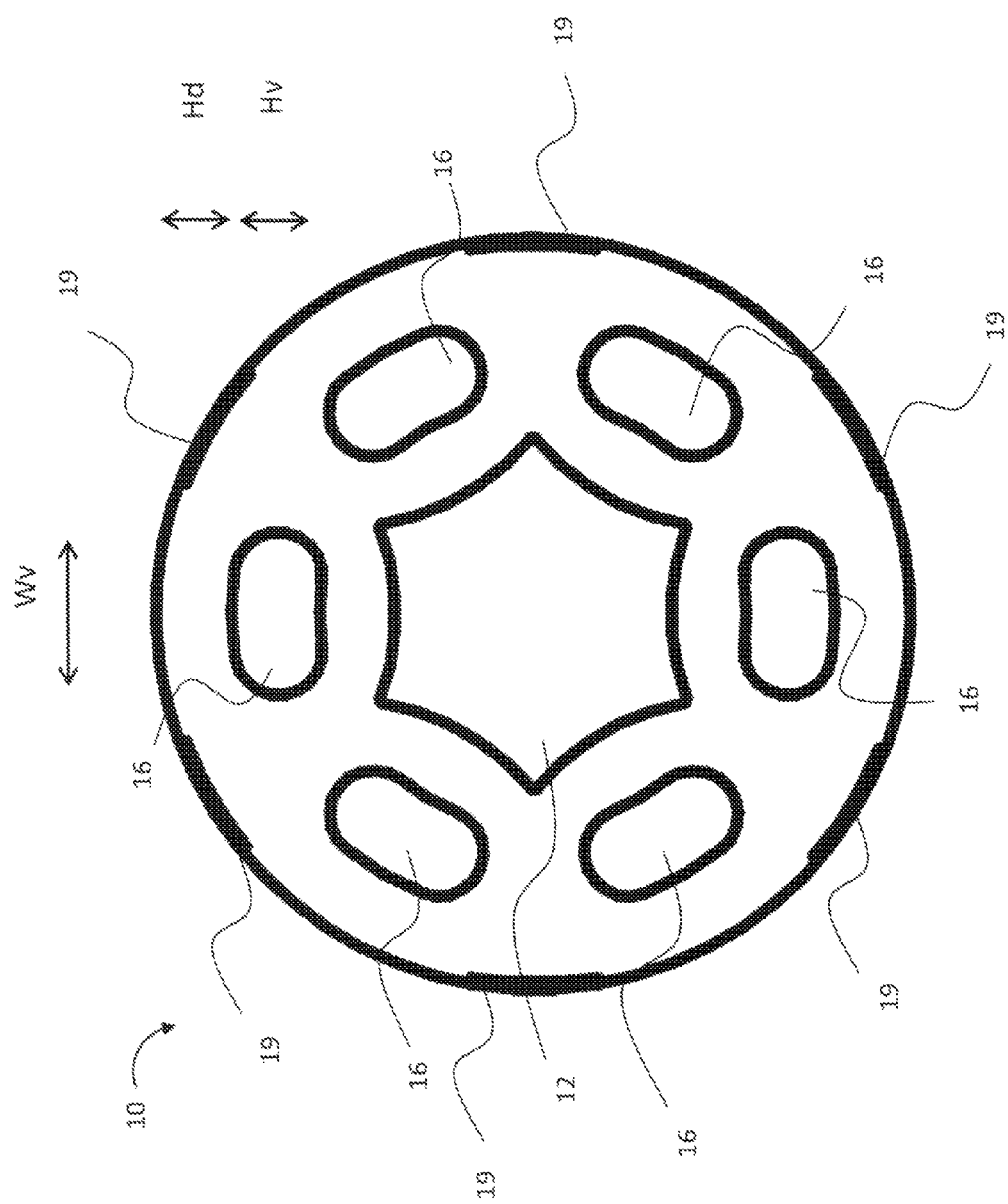
FIG. 2B is another simplified sectional illustration of the NGT of FIG. 1, taken along lines II-II in FIG. 1.

In another embodiment, distance Hd, as illustrated in FIG. 2B, between the perimeter of said vacuum lumen 16 and perimeter of said NGT 10 is between 0.2 mm-1 mm, between 0.3 mm-0.9 mm, between 0.4 mm-0.8 mm, between 0.5 mm-0.7 mm. In another embodiment, distance Hd is approximately 0.6 mm.

Main lumen 12 may be constructed from any suitable biocompatible material, such as but not limited to, polyurethane, silicone, polyvinyl chloride and many others. The vacuum lumens 16 may be constructed of similar materials, but alternatively may be constructed of medically safe metals, such as but not limited to, stainless steel, titanium alloys, NITINOL and others. Generally, without limitation, main lumen 12 may have a length in the range of 50 to 130 cm, with an outside diameter in the range of 5-12 Fr.

Main lumen 12 and vacuum lumens 16 may be constructed as one unit. Alternatively, vacuum lumens 16 may form a separate unit which is slid over main lumen 12 after insertion of main lumen 12 into the patient body. As another alternative, vacuum lumens 16 may be first introduced into the patient, and main lumen 12 may be slid in between vacuum lumens 16.

With reference to FIG. 1, each vacuum lumen 16 includes a vacuum sealing portion 24, which includes one or more suction ports 26. As shown in FIG. 1, some vacuum lumens 16 may have more suction ports than others. As shown in FIG. 3, upon application of vacuum generated by vacuum source 18, the inner wall of the esophagus is drawn by negative pressure towards and against suction ports 26 (the outer contour of NGT 10). The outer contour of NGT 10, at least at vacuum sealing portion 24, is preferably round (circular or oval), for better conforming to and sealing of the esophagus. In one embodiment, the vacuum sealing restricts at least 60% of the passage through the esophagus.

Pressure regulator 20 may be used to reduce or otherwise regulate the negative pressure generated by vacuum source 18. For example, pressure regulator 20 may be used to match the vacuum level generated by vacuum source 18 to the vacuum level needed in vacuum sealing portion 24. Such vacuum pressure may be, for example, between 0.5-50, 50-100, 100-200, 200-300, 300-400, 400-500, 500-600 or 600-700 mmHg. Different vacuum pressure values may be suitable to different patients and/or to different luminal structures into which the tube of the present invention is inserted.

Furthermore, vacuum lumen 16 includes a gastric decompression port as will be described in more detail hereinbelow. In some embodiments, vacuum lumen 16 including a gastric decompression port 23 also includes one or more suction ports 26, or alternatively is devoid of suction ports 26. Upon application of vacuum generated by vacuum source 18, a subject's abdomen (e.g., stomach and/or intestines) is decompressed to remove gastric gas, excessive reflux or the like. Pressure regulator 20 may apply vacuum pressure, for example, between 0.5-50, 50-100, 100-200, 200-300, 300-400, 400-500, 500-600 or 600-760 mmHg, required for gastric decompression. Those of skill in the art will recognize that the required vacuum pressure may be dependent on the amount of gas and/or excessive reflux being decomposed, as well as whether the vacuum pressure is applied in a constant or pulse manner. Valve 22 may provide variability to the applied vacuum pressure to vacuum lumen 16 which includes decompression port 23.

Valve 22 may be used to shift the vacuum between the different vacuum lumens 16 so that the suction level is not constant over time in the vacuum sealing portion 24, which may provide variability in how the esophagus wall is sucked in, and for how long.

NGT 10 may be provided with different numbers of vacuum sealing portions 24 and suction ports 26, and the vacuum to the sealing portions 24 may be regulated so as to create peristaltic movement or other oscillatory movement of the esophagus.

In accordance with an embodiment of the invention, one or more auxiliary suction ports 33 are provided proximal to vacuum sealing portion 24. Since vacuum sealing portion 24 seals off the esophagus, any oropharyngeal secretions, such as saliva, may accumulate above (i.e., proximal to) vacuum sealing portion 24. Auxiliary suction ports 33 may be used to suck and remove such secretions. Additionally or alternatively, one or more of vacuum lumens 16 may be used to evacuate liquids arriving from the patient's stomach. That is, if a reflux occurs, one or more of vacuum lumens 16 may withdrawn at least a portion of it, through suction ports 26, towards valve 22. There, the stomach contents may be collected inside a suitable reservoir and then discarded.

Vacuum source 18 is preferably activated following the insertion and localization of NGT 10 in the esophagus in order to reduce the risk of VAP, or other bacterial infections, by preventing or minimizing reflux food and liquid aspiration into the lungs.

Reference is now made to FIGS. 4A, 4B and 4C. FIG. 4A is a simplified, schematic illustration of a transparent front view of a portion of a nasogastric tube 50, constructed and operative in accordance with another non-limiting embodiment of the present invention. FIG. 4B is a simplified schematic illustration of a cross-section along line I-I of nasogastric tube 50 of FIG. 4A. FIG. 4C is a simplified schematic illustration of a cross-section along line II-II of nasogastric tube 50 of FIG. 4A. Nasogastric tube 50 is generally similar to nasogastric tube 10 of FIG. 1. The differences between nasogastric tube 10 and nasogastric tube 50 are detailed herein below. FIG. 4A shows a proximal portion of nasogastric tube 50 to be inserted into a patient's esophagus and with respect to it. Nasogastric tube 50 includes an additional upper portion, which is not shown, that is left outside of the patient's body and is coupled with, for example, vacuum source 18, pressure regulator 20 or valve 22. Nasogastric tube 50 includes main lumen 12 and six vacuum lumens 16, specifically denoted 16a, 16b, 16c, 16d, 16e and 16f. However, in other embodiments (not shown), a different number of vacuum lumens, such as four or more, may be used.

Nasogastric tube 50 further includes a decompression port(s) 23 located distal to the longitudinal location of suction ports 26b, and 26f, as shown in FIG. 4A. Decompression port(s) 23 are, in some embodiments, configured to be positioned inside a stomach or a duodenum.

Each vacuum lumen 16 includes a suction port 26, specifically denoted 26a, 26b, 26c, 26d, 26e and 26f correspondingly. Therefore, each of suction ports 26 is associated with one of lumens 16. Suction ports 26a, 26b, 26c, 26d, 26e and 26f are distributed along a longitudinal axis of nasogastric tube 50. Suction ports 26a, 26c and 26e are located above suction ports 26b, 26d and 26f along the longitudinal axis of nasogastric tube 50 and with respect to a patient's body. Such a longitudinal axis may be advantageously located within main lumen 12.

Reference is now made to FIGS. 4A, 4B and 4C. FIG. 4A is a simplified, schematic illustration of a transparent front view of a portion of a nasogastric tube 50, constructed and operative in accordance with another non-limiting embodiment of the present invention. FIG. 4B is a simplified schematic illustration of a cross-section along line I-I of nasogastric tube 50 of FIG. 4A. FIG. 4C is a simplified schematic illustration of a cross-section along line II-II of nasogastric tube 50 of FIG. 4A. Nasogastric tube 50 is generally similar to nasogastric tube 10 of FIG. 1. The differences between nasogastric tube 10 and nasogastric tube 50 are detailed herein below. FIG. 4A shows a proximal portion of nasogastric tube 50 to be inserted into a patient's esophagus and with respect to it. Nasogastric tube 50 includes an additional upper portion, which is not shown, that is left outside of the patient's body and is coupled with, for example, vacuum source 18, pressure regulator 20 or valve 22. Nasogastric tube 50 includes main lumen 12 and six vacuum lumens 16, specifically denoted 16a, 16b, 16c, 16d, 16e and 16f. However, in other embodiments (not shown), a different number of vacuum lumens, such as four or more, may be used. Nasogastric tube 50 further includes a decompression port(s) 23 located distal to the longitudinal location of suction ports 26b, and 26f, as shown in FIG. 4A. Decompression port(s) 23 are, in some embodiments, configured to be positioned inside a stomach or a duodenum.

Each vacuum lumen 16 includes a suction port 26, specifically denoted 26a, 26b, 26c, 26d, 26e and 26f correspondingly. Therefore, each of suction ports 26 is associated with one of lumens 16. Suction ports 26a, 26b, 26c, 26d, 26e and 26f are distributed along a longitudinal axis of nasogastric tube 50. Suction ports 26a, 26c and 26e are located above suction ports 26b, 26d and 26f along the longitudinal axis of nasogastric tube 50 and with respect to a patient's body. Such a longitudinal axis may be advantageously located within main lumen 12.

With specific reference to FIGS. 4B and 4C, FIG. 4B shows a cross-section of suction ports 26a, 26c and 26e. Suction ports 26a, 26c and 26e are peripherally distributed around main lumen 12 in the same longitudinal location with respect to main lumen 12 (i.e., along a longitudinal axis of nasogastric tube 50). FIG. 4C shows a cross-section of suction ports 26b, 26d and 26f. Suction ports 26b, 26d and 26f are peripherally distributed around main lumen 12 in the same longitudinal location with respect to main lumen 12, as shown in FIG. 4A. The longitudinal location of suction ports 26a, 26c and 26e is different from and located above the longitudinal location of suction ports 26b, 26d and 26f, as shown in FIG. 4A. Generally, without limitation, the distance between suction ports 26a, 26c and 26e and 26b, 26d and 26f is in the range of 50 to 250 mm, or 100 to 150 mm.

Therefore, for example, applying vacuum to vacuum lumens 16a or 16c or 16e or to any combination thereof, allows sealing of the esophagus against nasogastric tube 50 in different peripheral locations (i.e., depending on the vacuum lumens which are used) and in different levels (i.e., depending on how many vacuum lumen are used) but in a specific longitudinal location (denoted by line I-I with respect to nasogastric tube 50 in FIG. 4A). In order to allow maximal sealing of the esophagus, vacuum may be applied to vacuum lumens 16a, 16c and 16e together at the same time. Applying vacuum to vacuum lumens 16b or 16d or 16f or to a combination thereof, would result the same correspondingly but in different peripheral locations with respect to main lumen 12 (i.e., according to the peripheral locations of vacuum lumens 16b, 16d or 16f) and in particular, in a different longitudinal location along nasogastric tube 50, denoted by line II-II in FIG. 4A. Vacuum may be also applied to vacuum lumens located in different longitudinal locations along nasogastric tube 50 at the same time.

Hence, the location of the vacuum lumens within the nasogastric tube according to the present invention determines the peripheral location of the applied vacuum and the location of the suction ports determines the longitudinal location of the applied vacuum within the esophagus. It should be noted that the positioning of nasogastric tube 50 within the esophagus as performed by the attending caregiver should be also considered. Switching the applied vacuum between the vacuum lumens allows applying vacuum on the esophagus inner wall at different locations peripherally and longitudinally during time, thus diminishing or preventing damage to the esophagus tissue facing the suction ports.

Valve 22 may be used to switch the vacuum between one or more vacuum lumens 16. Valve 22 may be separately connected to each vacuum lumen 16 or, for example, connected to all of vacuum lumens 16 having suction ports 26 at the same longitudinal location with respect to nasogastric tube 50 together. Obviously, the latter setup of valve 22 allows less freedom in switching between vacuum lumens 16. Hence, valve 22 may be used to switch the applied vacuum after a time duration from one or more vacuum lumens located at specific peripheral and longitudinal locations to one or more vacuum lumens located at other peripheral locations or furthermore at other longitudinal locations. Such a switch may be preformed gradually in order to keep the esophagus sealed at least to some extent against nasogastric tube 50 during the switch.

Nasogastric tube 50 may include two or more vacuum lumens 16 which peripherally surround main lumen 12. At least two of vacuum ports 26 are located at different longitudinal locations along nasogastric tube 50 in order to allow a longitudinal location switch within the esophagus.

Suction ports 26 are elliptical but may be of any other form, such as circular. Suction ports 26 may include a graduated edging 28 to prevent or diminish damage to the esophagus tissue while an inner wall of the esophagus is pressed against suction ports 26. Graduated edging 28 is advantageously graduated in an obtuse angle. Graduated edging 28 may be graduated entirely or only include a graduated portion. Generally, graduated edging 28 may provide each of suction ports 26 with a concave shape, having an opening approximately in its middle.

Nasogastric tube 50 may be coupled with a manifold (not shown). The manifold may connect vacuum lumens 16 to valve 22 in a separate manner to allow vacuum application to one or more vacuum lumens 16. The manifold may be transparent in order to visually monitor backflow of gastric substances, such as bile.

In some embodiments, at least one suction port 26 may include two or more suction ports, successively arranged along a portion of a longitudinal axis of nasogastric tube 50.

Figure 5:
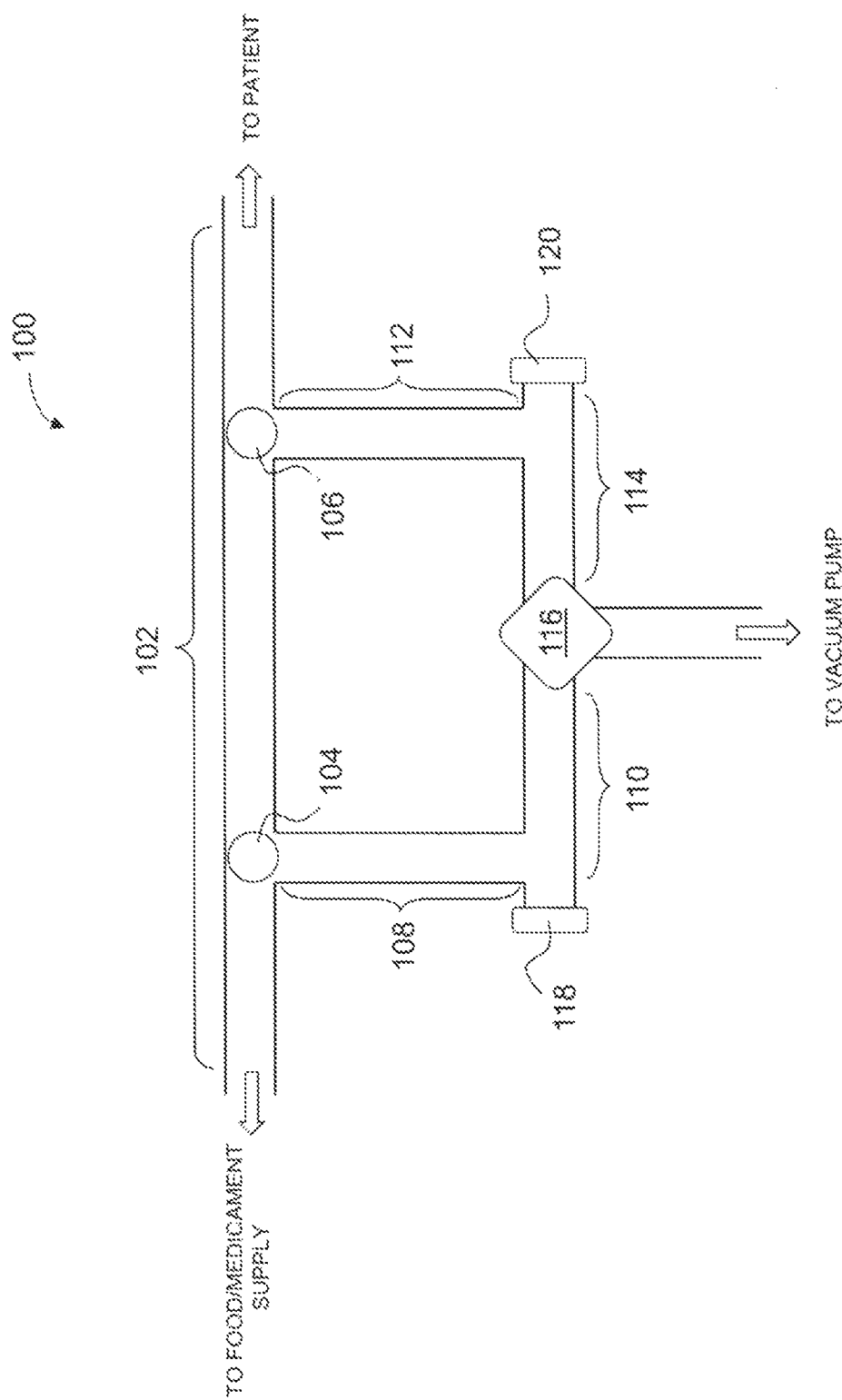
FIG. 5 is a schematic diagram of a manifold.

Reference is now made to FIG. 5, which shows a schematic diagram of a manifold 100, which, in accordance with some embodiments, serves as valve 22 of FIG. 1. Manifold 100 may be used to interconnect tubes extending between the patient, the food and/or medicament supply, and the vacuum source (e.g. a vacuum pump).

A main tube 102 may extend between the patient and the food and/or medicament supply. Main tube 102 may include, at manifold 100, two or more junctions 104 and 106. Junctions 104 and 106 may be used for alternating between different vacuum lumens or groups of vacuum lumens. That is, each of junctions 104 and 106 may interconnect different vacuum lumens or groups of vacuum lumens to the vacuum source. Junction 104, for example, may be connected to the vacuum source via a first tube (represented by tube portions 108 and 110). Junction 106, for example, may be connected to the vacuum source via a second tube (represented by tube portions 112 and 114). Tube portions 110 and 114 may be connected to the vacuum source through a selector 100. Selector 106 may have two possible states: In the first state, negative pressure from the vacuum source is channeled towards portion 110 and from there to junction 104. In the second state, negative pressure from the vacuum source is channeled towards portion 114 and from there to junction 106. In embodiments where more than two junctions are present (not shown), a selector may have a number of states corresponding to the number of junctions.

Optionally, manifold 100 may include one or more vacuum discharge ports, for releasing negative pressure from a certain vacuum lumen or a group of vacuum lumens after the negative pressure has been switched away from this lumen or group of vacuum lumens by selector 116. Two exemplary vacuum discharge ports 118 and 120 are shown in the figure. Optionally, the vacuum discharge ports 118 and 120 may each be a cap threadable at some point between selector 116 and junctions 104 and 106, respectively. After the caregiver has switched the vacuum from a first vacuum lumen (or a first group of lumens) to a second vacuum lumen (or a second group of lumens), he or she may use the suitable one of vacuum discharge ports 118 and 120 in order to immediately discharge the negative pressure from the first vacuum lumen (or the first group of lumens). This way, the inner wall of the esophagus, at the vacuum port(s) connected to the first vacuum lumen (or the first group of lumens), may be immediately released from the vacuum port(s) and tissue damage may be prevented or at least mitigated.

One method of using NGT 10 of the present invention includes the following steps, without limitation and not necessarily in sequential order:

a) introducing NGT 10 into the esophagus of the subject;
b) applying vacuum to one or more of the vacuum sealing portion(s) 24;
c) adjusting the vacuum level (which may be done before step a); and
d) after achieving a desired sealing of the esophagus wall to NGT 10, changing the vacuum intervals between the vacuum lumens 16, manually or automatically, such that NGT 10 remains intact to the esophagus.

e) applying, manually or automatically, vacuum to one or more of vacuum lumen 16 which include decompression port(s) 23.

In additional embodiments, said nasogastric tube has a length, and each of said plurality of suction ports is associated with a different one of said plurality of vacuum lumens, wherein said plurality of ports are distributed between at least two different locations along the length of said nasogastric tube. Distributing suction ports along the length of said nasogastric tube enables locally selective application of the vacuum within the esophagus. Thus, the location of the esophagus coupling to the tube may be changed in time in order to diminish tissue damage to the esophagus.

Figure 6:
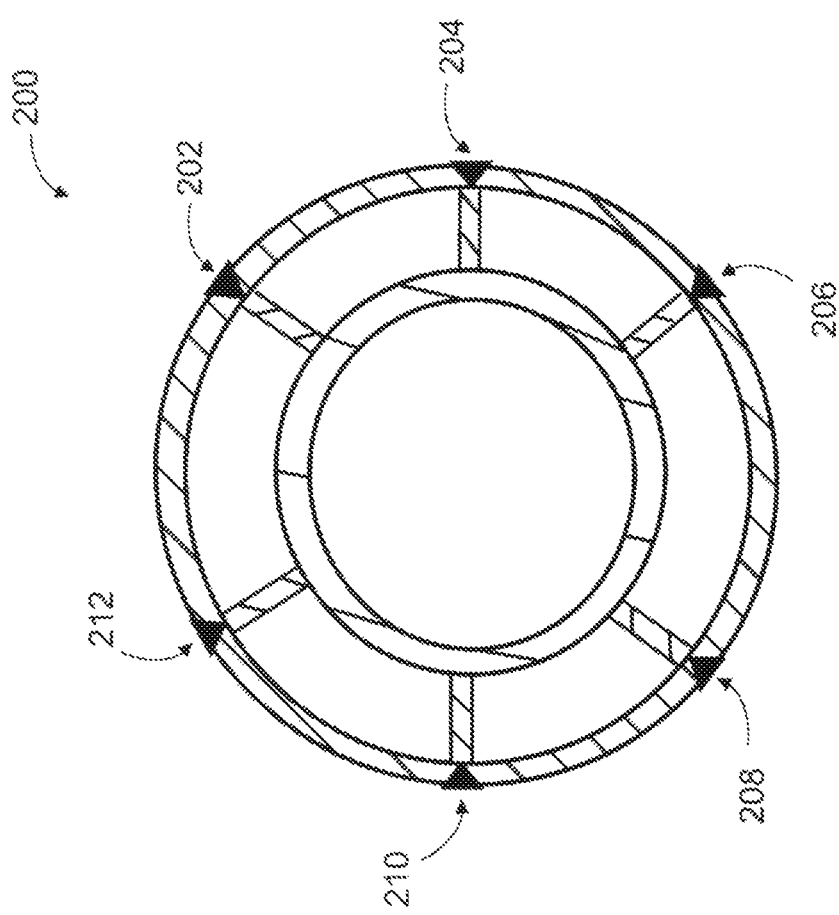
FIG. 6 is a cross section of a nasogastric tube.

Reference is now made to FIG. 6, which shows a cross section of a nasogastric tube 200, optionally similar to tube 10 (FIGS. 1-2) and/or to tube 50 (FIGS. 4A-4C). For simplicity of illustration, the cross section is shown at a portion of the tube which lacks any suction ports.

Tube 200 may include one or more radiopaque stripes, such as stripes 202-212, disposed along the longitudinal axis of the tube. Radiopaque stripes 202-212 may be visible, when tube 200 (or a portion thereof) is inside the patient, using X-ray imaging and/or other types of electromagnetic radiation imaging. That is, radiopaque stripes 202-212 are made of a radiodense material which inhibits the passage of some or all electromagnetic radiation, thereby creating a contrast in relation to more radiolucent body tissue and/or radiolucent portions of a medical device. Generally, if two or more parallel, longitudinal radiopaque stripes are present, the resulting electromagnetic radiation image may enable a better depth perception of the tube. This, since one or more of the stripes may be farther away from the imager than other one or more of the stripes. Furthermore, having two or more parallel, longitudinal radiopaque stripes may enable visualizing a situation in which the tube is twisted; this will result in a spiral-like image of the stripes.

An example of a suitable radiodense material is Barium sulfate, but those of skill in the art will recognize that other known radiodense materials may be used. In case Barium sulfate is used, its density in stripes 202-212 may be, for example, between 40-60%, between 60-80% or higher. The remainder percentage may be one or more filler materials.

Stripes 202-212, whether by virtue of their high-percentage Barium sulfate contents and/or their thickness, may endow tube 200 with a certain rigidity. This rigidity is to a degree which assists the caregiver in pushing the tube down the GI tract (or any other bodily lumen) on one hand, but still allows the tube to resiliently maneuver through the pertinent bodily lumen.

Optionally, one or more of stripes 202-212 may have an essentially triangular cross section, as shown in the figure. One apex of the triangle may be directed towards the inside of tube, and the base opposite to that apex may be directed towards the outside of the tube. In other embodiments (not shown), one or more of the stripes may have a rectangular cross-section, a circular cross-section, or an otherwise shaped cross-section.

Stripes 202-212 are optionally embedded, at least partially, in the outer wall of tube 200. Further optionally, stripes 202-212 may slightly protrude beyond the outside surface of the tube. For example, the protrusion may be by 50-100 micrometers, 100-150 micrometers, 150-250 micrometers, 250-400 micrometers or more. This protrusion may enable the caregiver holding tube 200 to get a better grip of the tube, especially when the tube has to be rotated. The protrusion may prevent the tube from slipping in the caregiver's hands while rotated.

Gastric Decompression

According to some embodiments, the NGT of the present invention is configured to perform as a feeding tube as well as a gastric decompression tube. Thus, the NGT enables administration of nutrients or drugs directly to a subject's stomach or intestines and simultaneously or interchangeably enables gastric decompression. In accordance with an embodiment, the invention provides a system comprising an NGT comprising a feeding mechanism, a suction mechanism configured to sealingly draw an inner wall of an esophagus thereagainst, and a gastric decompression mechanism.

In some embodiments, the gastric decompression mechanism comprises at least one gastric decompression port associated with at least one of said plurality of vacuum lumens, said at least one gastric decompression port being disposed distally to the at least two different locations along the length of said nasogastric tube. In another embodiment, the gastric decompression mechanism comprises at least at least one gastric decompression port associated with an additional at least one vacuum lumen, said at least one gastric decompression port being disposed distally to the at least two different locations along the length of said nasogastric tube. NGTs comprising gastric decompression mechanism and method for use of said NGTs are disclosed in PCT/IL2014/050576, the contents of which are incorporated herein by reference at their entirety.

In some embodiments, the suction mechanism is further configured to aspirate fluids from the esophagus. The suction mechanism and the gastric decompression mechanism are, in some embodiments, disposed (situated) and associated by one or more same lumens. In other embodiments, the suction mechanism and the gastric decompression mechanism are configured to perform by independent lumens. According to some embodiments, the peripheral (vacuum) lumens are configured to aspirate fluids such as gastric reflux from the esophagus. In some embodiments, said at least one suction port is configured to aspirate fluids from the esophagus. By virtue of applying vacuum to the peripheral lumens of the NGT described herein, the at least one suction port is used for sealingly drawing an inner wall of an esophagus thereagainst and interchangeably or simultaneously aspirate fluids from the esophagus. One skilled in the art will is well capable of determining the vacuum pressure to be applied for sealing the esophagus and/or aspirating fluids from the esophagus.

Figure 7A:
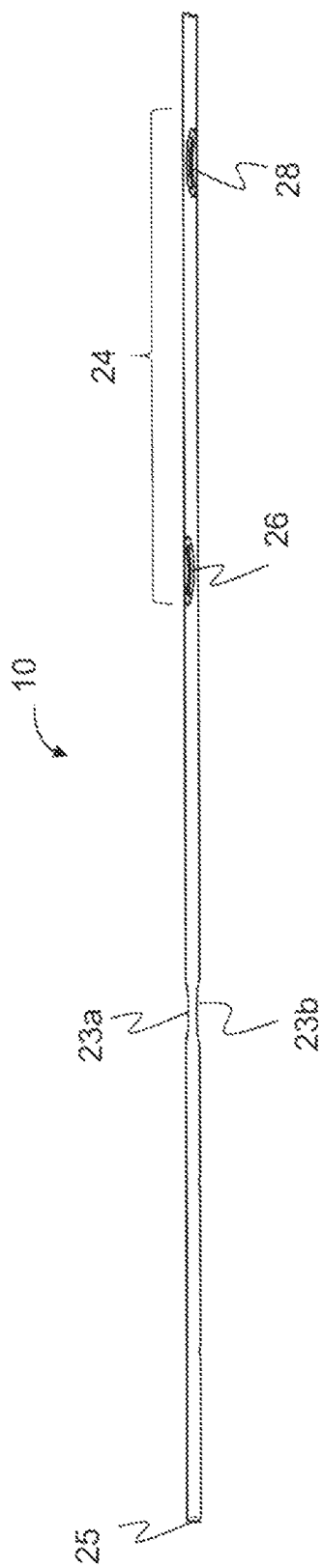
FIG. 7A is a simplified, schematic illustration of a portion of a nasogastric tube in accordance with a non-limiting embodiment of the present invention.
Figure 7B:
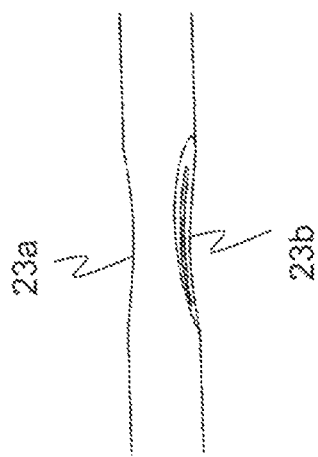
FIG. 7B is a simplified enlarged illustration of a portion of the nasogastric tube comprising the decompression ports, in accordance with a non-limiting embodiment of the present invention.

Reference is now made to FIGS. 7A and 7B. FIG. 7A illustrates a simplified, schematic illustration of a portion of an NGT 10, constructed and operative in accordance with a non-limiting embodiment of the present invention. FIG. 7B is a simplified and enlarged illustration of a distal portion of the NGT comprising one or more gastric decompression ports. NGT 10 includes, for example, a vacuum sealing portion 24 comprising two suction ports 28 and 26 distributed between two different locations along the length of NGT 10. NGT 10 further includes one or more gastric decompression ports 23a and 23b disposed distally to the vacuum sealing portion 24. Typically, the one or more gastric decompression ports 23a and 23b are configured to be positioned inside a stomach and/or a proximal duodenum.

Generally, without limitation, the distance between one or more gastric decompression ports 23 to at least one suction port is in the range of 50 to 200 mm.

The one or more gastric decompression port(s) 23 is associated with at least one of vacuum lumen 16 (not shown). In some embodiments, the one or more gastric decompression port(s) 23 is associated with a vacuum lumen 16 which comprises one or more suction ports 26. In other embodiments, the one or more gastric decompression port(s) 23 is associated with at least one additional vacuum lumen 16 (such as a vacuum lumen 16 devoid of suction ports 26). Gastric decompression port(s) 23 may be configured to be positioned inside a stomach. Gastric decompression port(s) 23, in another embodiment, may be configured to be positioned inside a proximal duodenum. Gastric decompression port 23 is, in some embodiments, disposed distally to vacuum sealing portion 24 (and suction ports 28 and 26). Decompression port(s) 23 may be elliptical or of any other form, such as circular.

NGT 10 further includes one or more feeding port 25 at the distal end of main lumen 12. In additional embodiments, such as for simultaneous feeding and decompression, the one or more feeding ports 25 are distal to the one or more gastric decompression ports 23. Feeding port 25 may be configured to be positioned in the stomach or in the duodenum. Generally, without limitation, the distance between one or more gastric decompression ports 23 to at least one feeding port is in the range of 50 to 300 mm, or in the range of 100 to 200 mm.

In one embodiment, the one or more gastric decompression port(s) 23 are configured to be positioned in a position selected from a distal esophagus (i.e., distal to vacuum sealing portion 24), inside a stomach, proximal duodenum, or a combination thereof. In embodiments wherein gastric decompression port(s) 23 are configured to be positioned in the proximal duodenum, feeding port 25 may be configured to be positioned in a distal duodenum.

Vacuum lumen 16 comprising a decompression port 23 may be constructed of similar materials to vacuum lumen 16 comprising suction ports 26, but alternatively may be constructed of medically safe metals, such as but not limited to, stainless steel, titanium alloys, NITINOL and others.

As known to one skilled in the art, the system described herein may further comprise a guiding probe (e.g., a stylet) for inserting the NGT to a subject. Said guiding probe is typically is removed after confirming the correct placement of the NGT.

A method of using NGT 50 of the present invention may include the following steps, without limitation and not necessarily in sequential order:
 a) introducing the NGT into an esophagus of a patient;
 b) applying vacuum to one or more decompression ports; and
 c) applying vacuum to one or more suction ports interchangeably between the differently located suction ports so as to sealingly draw an inner wall of the esophagus thereagainst each time in a different location along the esophagus.

The vacuum may be applied to vacuum lumen(s) comprising one or more decompression ports in a constant manner or alternatively in timely intervals. As such, vacuum may be applied to the decompression ports prior to, during or after a patient is being fed by the NGT described herein. In additional embodiments, vacuum may be applied to the decompression ports according to the subject request, such as in result to abdominal discomfort, including but not limited to, excessive gastric gas or the like.

The vacuum may be applied to one or more vacuum lumens each time, and in each time to vacuum lumens which include suction ports peripherally distributed around the same location along a longitudinal axis of the NGT (for example, vacuum lumens 16a and 16c or vacuum lumens 16b, 16d and 16f of FIGS. 4A, 4B and 4C) or peripherally distributed around different locations along a longitudinal axis of the NGT (for example, vacuum lumens 16a and 16d of FIGS. 4A, 4B and 4C).

The interchanging between the vacuum lumens to which a vacuum is applied may be performed at various manners, for example, it may be performed once or more per patient while each location change may be performed once in a constant or variable period of time, all according to the caregiver discretion regarding the specific patient.

In some embodiments, said vacuum is applied to one or more suction ports interchangeably between the differently located suction ports so as to sealingly draw an inner wall of the esophagus thereagainst each time in a different location along the esophagus. The vacuum may be applied to one or more vacuum lumens each time, and in each time to vacuum lumens which include suction ports peripherally distributed around the same location along a longitudinal axis of the NGT or peripherally distributed around different locations along a longitudinal axis of the NGT. The interchanging between the vacuum lumens to which a vacuum is applied may be performed at various manners, for example, it may be performed once or more per patient while each location change may be performed once in a constant or variable period of time, all according to the caregiver discretion regarding the specific patient.

The method may further include the step of regulating the vacuum so that a suction level is not constant over time in the suction ports. The vacuum may be regulated to the vacuum ports so as to create peristaltic movement or other oscillatory movement of the esophagus.

In some embodiments, the vacuum may be applied such that to restricts at least 60% of passage through the esophagus.

Nasogastric tube 10 may be coupled with a manifold (not shown). The manifold may connect vacuum lumens 16 to valve 22 in a separate manner to allow vacuum application to one or more vacuum lumens 16. The manifold may be transparent in order to visually monitor backflow of gastric substances, such as bile.

The method may further include the step of visually monitoring a transparent manifold which couples the vacuum lumens with a valve for backflow of gastric substances, such as bile.

In some embodiments of the present invention, the present invention may be utilized to insert one or more probes through main lumen 12, through one or more of vacuum lumens 16 and/or through a different, dedicated lumen (not shown) into the patient's body. Such probes may include, for example: a temperature sensor, an electromagnetic radiation sensor, a pH sensor, an image sensor, a fiber optic, an ultrasound probe, an OCT (optical coherence tomography) probe, a mini MRI (magnetic resonance imaging) probe, etc.

The NGT may include one or more radiopaque stripes 19 disposed along the longitudinal axis of the tube. Radiopaque stripes may be visible, when tube (or a portion thereof) is inside the patient, using X-ray imaging and/or other types of electromagnetic radiation imaging. That is, radiopaque stripes are made of a radiodense material which inhibits the passage of some or all electromagnetic radiation, thereby creating a contrast in relation to more radiolucent body tissue and/or radiolucent portions of a medical device. Generally, if two or more parallel, longitudinal radiopaque stripes are present, the resulting electromagnetic radiation image may enable a better depth perception of the tube. This, since one or more of the stripes may be farther away from the imager than other one or more of the stripes. Furthermore, having two or more parallel, longitudinal radiopaque stripes may enable visualizing a situation in which the tube is twisted; this will result in a spiral-like image of the stripes. An example of a suitable radiodense material is Barium sulfate, but those of skill in the art will recognize that other known radiodense materials may be used. In case Barium sulfate is used, its density in stripes may be, for example, between 40-60%, between 60-80% or higher. The remainder percentage may be one or more filler materials.

In some embodiments, said main lumen comprises at least one feeding port at or adjacent to the distal end of said nasogastric tube. As used herein "adjacent to the distal end of said nasogastric tube" refers to at most 10 cm, at most 9 cm, at most 8 cm, at most 7 cm, at most 6 cm, at most 5 cm, at most 4 cm, at most 3 cm, at most 2 cm, at most 1 cm, at most 0.75 cm, at most 0.5 cm, at most 0.25 cm from the distal end of said nasogastric tube. Each possibility is a separate embodiment of the present invention.

The present invention is based, in part, on finding that a unique structure of the suction unit(s) of said NGT allows the coupling of the esophagus to the tube while preventing the drawing of said tissue into the vacuum lumen, when vacuum force is applied. Thus, the NGT disclosed herein advantageously prevents reflux along the esophagus while refraining from causing tissue damage.

Figure 8A:
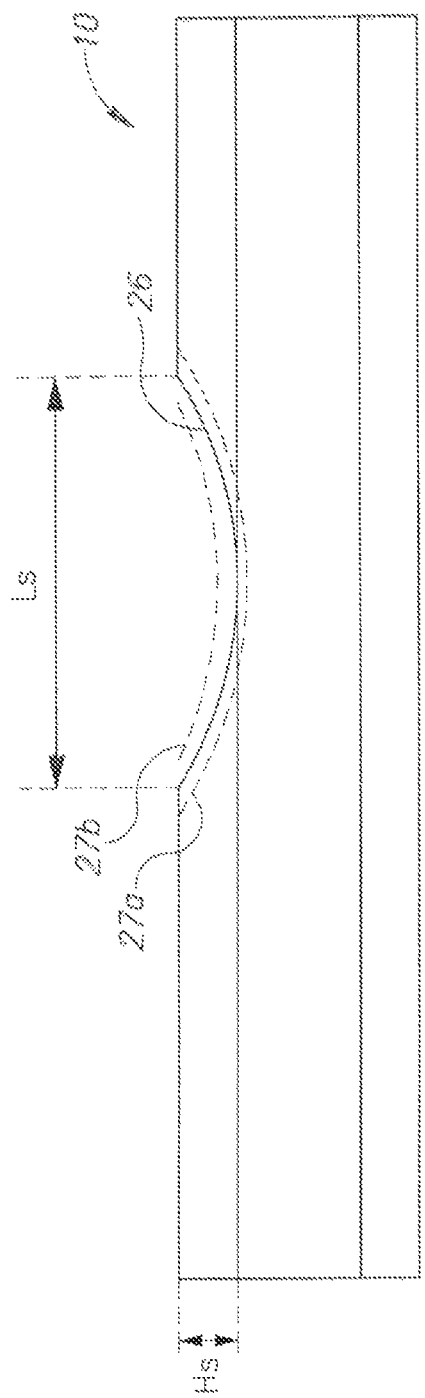
FIG. 8A is a simplified, schematic illustration of a side view of a portion of a nasogastric tube, constructed and operative in accordance with another embodiment of the present invention.
Figure 8B:
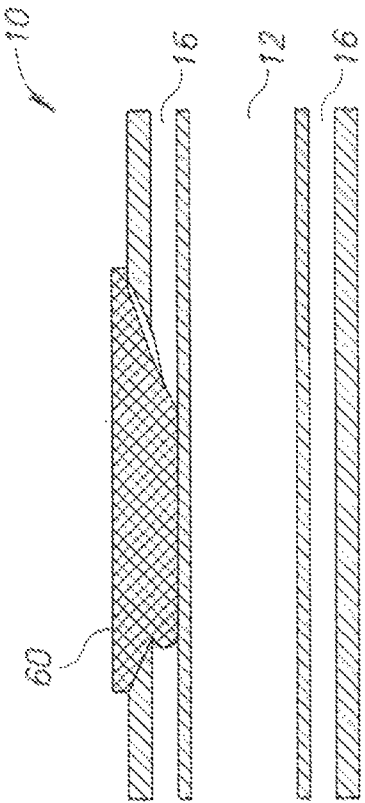
FIG. 8B is a simplified schematic illustration of a transparent side view of a portion of a nasogastric tube, depicting a tissue being drawn into the vacuum lumen.

Reference is made to FIG. 8B depicting a longitudinal section of an embodiment of an NGT of the invention, having a main lumen and one vacuum lumen comprising a suction unit (or suction port). For simplicity of discussion, only one suction port is shown while it should be appreciated that more than one suction port may be included. FIG. 8B further depicts a tissue, e.g., esophagus tissue, being pulled in by the applied vacuum force. It will be appreciated by a person skilled in the art that in order to couple the tissue to the tube, the tissue should reach the lumen base. Nevertheless, clinical trials have shown tissue damage in cases when the applied vacuum sucked the tissue into the vacuum lumen (i.e., beyond the suction port). Thus, the NGT described herein provides specific and unique structure of one or more suction ports and/or of the vacuum lumen which substantially prevent tissue damage.

In some embodiments, a nasogastric tube of the invention comprises at least one vacuum lumen comprising at least one suction port for sealingly drawing an inner wall of an esophagus thereagainst, said at least one suction port has a concavity whose longitudinal cross-section has a shape delimited between (i) a first arc of a first circle, the first arc having a length of 25 millimeters and a height of 1.5 millimeters, and (ii) a second arc of a second circle, the second arc having a length of 15 millimeters and a height of 1 millimeter.

Reference is now made to FIG. 8A. FIG. 8A is a simplified, schematic illustration of a side view of a portion of a nasogastric tube, constructed and operative in accordance with a non-limiting embodiment of the present invention. Nasogastric tube 10 is generally similar to nasogastric tube 10 of FIG. 1 as detailed hereinbelow, and for simplicity only one suction port 26 is shown. Nasogastric tube 10 comprises suction port(s) 26 having a concavity whose longitudinal cross-section has a shape delimited between a first arc of a first circle 27a and a second arc of a second circle 27b.

In some embodiments, the first arc of a first circle has a length of 25 millimeters and a height of 1.5 millimeters. In some embodiments, said first arc of a first circle has a length of 24 millimeters, 23 millimeters, 22 millimeters or 21 millimeters and a height of 1.5 millimeters. In another embodiment, said first arc of a first circle has a length of 25 millimeters, 24 millimeters, 23 millimeters, 22 millimeters or 21 millimeters and a height of 1.4 millimeters. In another embodiment, said first arc of a first circle has a length of 25 millimeters, 24 millimeters, 23 millimeters, 22 millimeters or 21 millimeters and a height of 1.3 millimeters. In another embodiment, said first arc of a first circle has a length of 25 millimeters, 24 millimeters, 23 millimeters, 22 millimeters or 21 millimeters and a height of 1 millimeters.

In another embodiment, the second arc of a second circle has a length of 15 millimeters and a height of 1 millimeter. In another embodiment, said second arc of a second circle has a length of 15 millimeters, 16 millimeters, 17 millimeters, 18 millimeters, 19 millimeters or 20 millimeters and a height of 1 millimeters. In another embodiment, said second arc of a second circle has a length of 15 millimeters, 16 millimeters, 17 millimeters, 18 millimeters, 19 millimeters or 20 millimeters and a height of 1.1 millimeters. In another embodiment, said second arc of a second circle has a length of 15 millimeters, 16 millimeters, 17 millimeters, 18 millimeters, 19 millimeters or 20 millimeters and a height of 1.2 millimeters.

In another embodiment, the at least one suction port 26 has a concavity having an arc having a length of 18 mm, 19 mm, 20 mm, 21 mm or 22 mm, wherein each possibility represents a separate embodiment of the present invention. In exemplary embodiments, said arc has a length between 20 mm-21 mm, 20.1 mm, 20.3 mm or approximately 20.12 mm.

Said concavity of said suction port may alternatively be defined by a height Hs and Ls as depicted in FIG. 8A. In some embodiments, the one or more suction ports have a maximum concavity Hs of 1.5 mm as measured over a length Ls of 20 mm. In some embodiments, the one or more suction ports have a maximum concavity Hs of 1.4 mm as measured over a length Ls of 20 mm. In some embodiments, the one or more suction ports have a maximum concavity Hs of 1.3 mm as measured over a length Ls of 20 mm. In some embodiments, the one or more suction ports have a maximum concavity Hs of 1.2 mm as measured over a length Ls of 20 mm. In another embodiment, said length Ls is 18 mm, 19 mm, 20 mm, 21 mm or 22 mm, wherein each possibility represents a separate embodiment of the present invention.

Reference is made to FIG. 8B depicting a transparent longitudinal section of an embodiment of an NGT of the invention. NGT 10 comprises a main lumen 12 and one or more vacuum lumen(s) 16 comprising a suction port. When negative pressure is applied (i.e. vacuum), tissue 60 (e.g., esophagus tissue), is pulled in to the suction port. FIG. 8B shows as a non-limiting embodiment a cause for issue damage in cases when the applied vacuum sucks the tissue into the vacuum lumen 16 (i.e., beyond the suction port). In some embodiments, the NGT described herein provides specific and unique structure of one or more suction ports and/or of the vacuum lumen 26 which substantially prevent drawing of tissue in to the vacuum lumen 16 and thus prevent tissue damage.

Suction ports 26 are in some embodiments substantially rectangular shaped, such as rectangular with rounded corners as depicted in FIG. 2B. In other embodiments, suction ports 26 are elliptical or circular.

In some embodiments, at least one suction port 26 may include two or more suction ports, successively arranged along a portion of a longitudinal axis of nasogastric tube 10.

Reference is now made to FIGS. 9A-B which illustrates an imaging system 900 provided with the nasogastric tube 10 for capturing and rendering one or more images of an area accessible by said nasogastric tube, in accordance with an embodiment.

Imaging system 900 may comprise a camera 902, and an orientation adjustor 906 (not shown) that are both disposed at a distal end of NGT 10, as well as a camera cable 904 connecting camera 902 and orientation adjustor 906 to a processing unit 908 disposed at a proximal end of NGT 10. Camera 902 may include one or more optical lenses mounted to a sensor, such as a complementary metal-oxide semiconductor (CMOS) or charged coupled device (CCD) sensor, and may capture one or more images of an area accessible by NGT 10, such as the esophagus, stomach and/or intestines. Images captured by camera 902 may be communicated to video processing unit 908 via camera cable 904. Camera cable 904 may additionally provide power and a control signal from processing unit 908 to any of camera 902 and orientation adjustor 906.

Imaging system 900 may provide an illuminator 910, such as one or more LED light sources or fiber-optic light source, at a distal end of nasogastric tube 10 to illuminate an area surrounding the camera 902, enabling camera 902 to capture the images. Illuminator 910 may powered and controlled by processing unit 908 via a light cable 912 connecting illuminator 910 to processing unit 908.

In an embodiment, camera 902 and illuminator 910 may be sealed to prevent damage from inner bodily fluids.

Camera 902 and/or illuminator 910 may be affixed to NGT 10 via any suitable means, such as via an adhesive to an exterior side of NGT 10, or within any lumens provided with NGT 10. In one embodiment, camera 902 and/or illuminator 910 may be affixed to the distal end of NGT 10 via a threaded connection, mechanical clip or spring joint, allowing for easy attachment, detachment, or replacement. Camera cable 904 and light cable 912 may be housed in one or more lumens provided with NGT 10, such as any of the vacuum lumens provided with NGT 10, or in main lumen 12, in a manner to isolate the cables from any bodily fluids present in or around NGT 10 to prevent their becoming wet or otherwise damaged. Alternatively the cables may be insulated and affixed externally to NGT 10. Camera cable 902 and light cable 912 may be isolated from each other to reduce noise. Camera cable 902 and/or light cable 912 may be compatible with any suitable communications protocol, such as RS232 protocol, USB, RS-422, firewire, camera link, or gigabit Ethernet protocol communication line, to name a few.

Video processing unit 908 may be disposed at a proximal end of NGT 10 and may transmit via any of camera cable 902 and light cable 912 a control signal to control features such automatic gain control (AGC), exposure control, on/off switch, and/or color balance for imaging unit 902 and/or illuminator 910. In one embodiment, video processing unit 908 may enable controlling the orientation of camera 902 with a control signal transmitted via camera cable 904 to orientation adjustor 906, to enable capturing images from different angles within the esophagus, stomach and/or intestines.

Video processing unit 908 may receive and store the captured images via camera cable 904, and process and render the images. A display screen 914 may be provided with video processing unit 906 to display or otherwise render the images captured by camera 902 for viewing by a user. The user may apply one or more control signals, via a control panel 916 provided with video processing unit 908, to control any of camera 902 and/or illuminator 910 in response to the images displayed on display screen 914.

In another embodiment a work channel may be disposed with nasogastric tube 10 to provide a tool to an area accessible by nasogastric tube 10, such as for removing a blockage detected by camera 902.

In another embodiment, an irrigation lumen may be disposed with nasogastric tube 10 to irrigate a blocked region that is accessible by nasogastric tube 10.

A cap 918 may provided at the distal end of NGT 10 to enclose and insulate any of the components of imaging system 900. Cap 918 may be disposed with an opening for camera 902, another opening for illuminator 910, and at least a third opening for any of a feeding tube and/or vacuum lumens provided with NGT 10.

A method for inserting NGT 10 of the present invention may include the following steps, without limitation and not necessarily in sequential order:

the distal end of NGT 10 may be introduced into the esophagus of the patient by an operator;
one or more images of an area illuminated by the illuminator may be captured by the camera;
the captured images may be transmitted to a processing unit;
the processed images may be rendered on a display unit;
the operator may monitor the progress of the distal end of the tube via the rendered images;
the operator may adjust the positioning of the tube in response to the rendered images;
the operator may adjust the orientation of the camera in response to the rendered images;
the operator may adjust the intensity of the illuminator in response to the rendered image.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A system comprising: a nasogastric tube comprising: (a) a main lumen having one or more proximal connectors for connecting to a source of substances or pressure, (b) at least four vacuum lumens circumferentially surrounding said main lumen, (c) at least four suction ports for circumferentially and sealingly drawing an inner wall of an esophagus thereagainst, each of said at least four suction ports associated with a different one of said at least four vacuum lumens, wherein said at least four suction ports are distributed between at least two different locations along a longitudinal axis of said nasogastric tube; and an imaging system for capturing and rendering one or more images of an area accessible by said nasogastric tube, wherein said imaging system comprises: (d) a camera that is disposed at a distal end of said nasogastric tube for capturing said images; (e) an illuminator that is disposed at said distal end of said nasogastric tube for illuminating an area surrounding said camera; (f) a processing unit that is provided at a proximal end of said nasogastric tube, configured to receive and process said captured images, render said processed images on a display screen, and provide a camera control signal to control said camera and a light control signal to control said illuminator; and (g) a valve connected to said at least four vacuum lumens, said valve configured to shift an applied vacuum between different ones of said at least four vacuum lumens, thereby: varying how said inner wall of the esophagus is circumferentially and sealingly drawn, and changing the vacuum intervals between said different ones of said at least four vacuum lumens.

2. The system according to claim 1, further comprising:
a camera cable connecting said camera to said processing unit, wherein said images and said camera control signal are transmitted via said camera cable; and
a light cable connecting said illuminator to said processing unit, wherein said light control signal is transmitted via said light cable.

3. The system of claim 2, wherein said camera cable and said light cable are housed in any of said at least four vacuum lumens.

4. The system according to claim 1, further comprising a vacuum source connected to said at least four vacuum lumens.

5. The system according to claim 1, further comprising a manifold configured to connect said at least four vacuum lumens to said valve.

6. The system according to claim 5, wherein said manifold is transparent.

7. The system of claim 1, further comprising an orientation adjustor controlling the orientation of said camera.

8. The system of claim 1, further comprising a control panel for applying said camera control signal and said light control signal.

9. The system according to claim 1, wherein said main lumen and said at least four vacuum lumens are constructed as one unit.

10. The system according to claim 1, wherein said at least four vacuum lumens are a separate unit from said main lumen, and wherein said at least four vacuum lumens are slidable relative to said main lumen.

11. The system according to claim 1, wherein said main lumen and said at least four vacuum lumens are arranged as concentrically arranged conduits.

12. The system according to claim 1, further comprising one or more auxiliary suction ports proximal to said at least four suction ports.

13. The system according to claim 1, wherein each of said at least four suction ports comprises a graduated edging.

14. The system according to claim 1, wherein said at least four vacuum lumens comprise at least six vacuum lumens.

15. The system according to claim 1, wherein at least one of said at least four suction ports comprises two or more suction ports, successively arranged along a portion of a longitudinal axis of said nasogastric tube.

16. The system according to claim 1, wherein said nasogastric tube further comprises two or more longitudinal radiopaque stripes.

17. The system according to claim 1, wherein said two or more longitudinal radiopaque stripes are embedded in an outer wall of said nasogastric tube.

18. The system according to claim 1, further comprising at least one gastric decompression port associated with an additional at least one vacuum lumen, wherein said at least one gastric decompression port is disposed distally to said at least two different locations along a length of said nasogastric tube.

19. The system according to claim 1, wherein said at least four suction ports are positioned on a circumference extension of said main lumen and have a concavity whose longitudinal cross-section have a shape delimited between (i) a first arc of a first circle, the first arc having a length of 25 millimeters and a height of 1.5 millimeters, and (ii) a second arc of a second circle, the second arc having a length of 15 millimeters and a height of 1 millimeter.

20. The system of claim 1, wherein each of said at least four vacuum lumens is substantially rectangular shaped.

21. The system of claim 1, wherein each of said at least four vacuum lumens has a width-height aspect ratio of 1:1 to 3:1.

22. The system of claim 1, wherein each of said at least four vacuum lumens has a height of 0.3-0.8 mm.

23. The system of claim 1, wherein each of said at least four vacuum lumens has a width of at most 1.5 mm.

24. A method comprising: introducing a nasogastric tube into an esophagus of a patient, said nasogastric tube comprising a main lumen having one or more proximal connectors for connecting to a source of substances or pressure, four or more vacuum lumens circumferential to said main lumen, four or more suction ports, each of said four or more suction ports associated with a different one of said four or more vacuum lumens, wherein said four or more suction ports are distributed between at least two different locations along said nasogastric tube, and a camera and illuminator disposed at a distal end of said nasogastric tube; introducing a valve connected to said at least four vacuum lumens, said valve configured to shift an applied vacuum between different ones of said at least four vacuum lumens; applying vacuum interchangeably to said four or more vacuum lumens so as to circumferentially sealingly draw an inner wall of an esophagus thereagainst, each time in a different location along said esophagus, wherein said valve varies how said inner wall of the esophagus is circumferentially and sealingly drawn and changes the vacuum intervals between said different ones of said at least four vacuum lumens; capturing an image by said camera of an area illuminated by said illuminator; transmitting said captured image to a processing unit; and processing and rendering said image on a display unit.

25. The method of claim 24, further comprising adjusting a positioning of said nasogastric tube in response to said rendered image.

26. The method of claim 24, further comprising adjusting an orientation of said camera via an orientation adjustor, in response to said rendered image.

27. The method of claim 24, further comprising adjusting an intensity of said illuminator, in response to said rendered image.

28. The method according to claim 24, further comprising regulating the vacuum so that a suction level is not constant over time.

29. The method according to claim 24, further comprising regulating vacuum to said four or more suction ports of said four or more vacuum lumen, so as to create peristaltic movement or other oscillatory movement of the esophagus.

* * * * *